United States Patent
Georgeson

(10) Patent No.: US 10,894,100 B2
(45) Date of Patent: *Jan. 19, 2021

(54) CLEANING AND DISINFECTING CRADLE FOR HEAD WORN ITEMS

(71) Applicant: Cleanbox Technology, Inc., Carlsbad, CA (US)

(72) Inventor: David Allen Georgeson, Vista, CA (US)

(73) Assignee: Cleanbox Technology, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/808,292

(22) Filed: Mar. 3, 2020

(65) Prior Publication Data

US 2020/0197548 A1 Jun. 25, 2020

Related U.S. Application Data

(63) Continuation of application No. 16/409,726, filed on May 10, 2019, now abandoned, which is a
(Continued)

(51) Int. Cl.
*A61L 2/10* (2006.01)
*A61L 2/24* (2006.01)
(Continued)

(52) U.S. Cl.
CPC ............... *A61L 2/0047* (2013.01); *A61L 2/10* (2013.01); *A61L 2/24* (2013.01); *A61L 12/063* (2013.01);
(Continued)

(58) Field of Classification Search
CPC . A61L 2/0047; A61L 2/10; A61L 2/24; A61L 2202/122; A61L 12/063; G06T 19/006
See application file for complete search history.

(56) References Cited

U.S. PATENT DOCUMENTS 5,160,699 A * 11/1992 Siegal .................. A61L 2/10
250/455.11
8,597,588 B1 * 12/2013 Trabalka .............. A61L 2/10
422/300
(Continued)

FOREIGN PATENT DOCUMENTS

KR   20160109597 A * 9/2016
KR   20160109597 A   9/2016

OTHER PUBLICATIONS

ISA/US—Notification with International Search Report and Written Opinion dated Dec. 1, 2017 for related International Application No. PCT/US2017/054342, 7 pgs.

*Primary Examiner* — David E Smith
(74) *Attorney, Agent, or Firm* — Incubate IP; Randy R. Micheletti

(57) ABSTRACT

Some embodiments of the present disclosure include a disinfecting/cleaning box for disinfecting and cleaning a head worn item. The disinfecting/cleaning box may include a chamber having an inner volume sufficient to accommodate the head worn item; and an ultraviolet (UV) light source provided in the chamber, wherein the UV light source is disposed to shine UV light onto a surface of the head worn item.

13 Claims, 4 Drawing Sheets

Related U.S. Application Data continuation of application No. 15/720,037, filed on Sep. 29, 2017, now Pat. No. 10,328,166.

(60) Provisional application No. 62/402,827, filed on Sep. 30, 2016.

(51) Int. Cl.
*A61L 2/00* (2006.01)
*A61L 12/06* (2006.01)
*G06T 19/00* (2011.01)

(52) U.S. Cl.
CPC ....... *A61L 2202/122* (2013.01); *G06T 19/006* (2013.01)

(56) References Cited

U.S. PATENT DOCUMENTS

| | | |
|---|---|---|
| 8,703,051 B2 | 4/2014 | Trabalka et al. |
| 9,107,973 B1 | 8/2015 | Robinson et al. |
| 10,328,166 B2 * | 6/2019 | Georgeson ............ A61L 2/0047 |
| 2005/0191505 A1 | 9/2005 | Akarsu et al. |
| 2011/0243789 A1 * | 10/2011 | Roberts .................... A61L 2/10 |
| | | 422/24 |
| 2015/0382123 A1 | 12/2015 | Jobani |
| 2016/0303265 A1 * | 10/2016 | Coles ........................ A61L 2/24 |

* cited by examiner

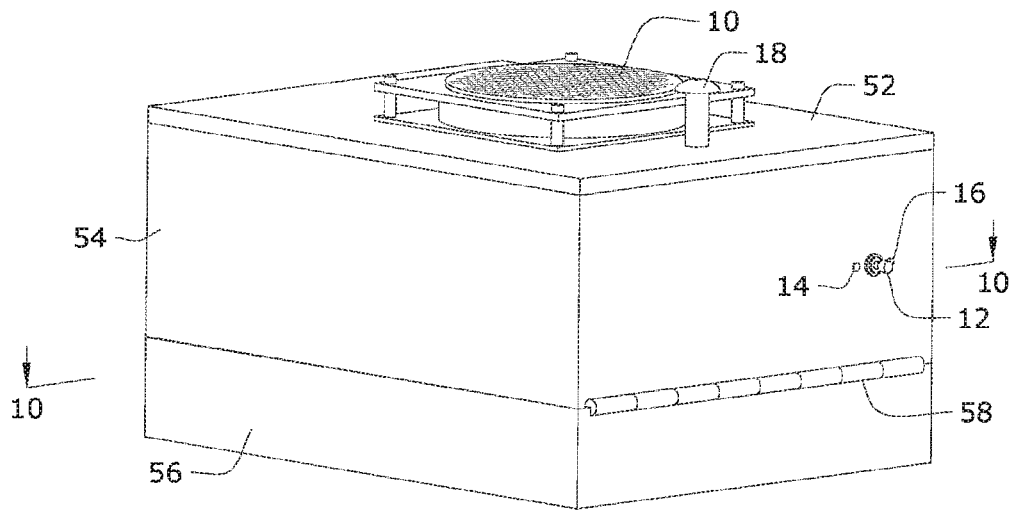
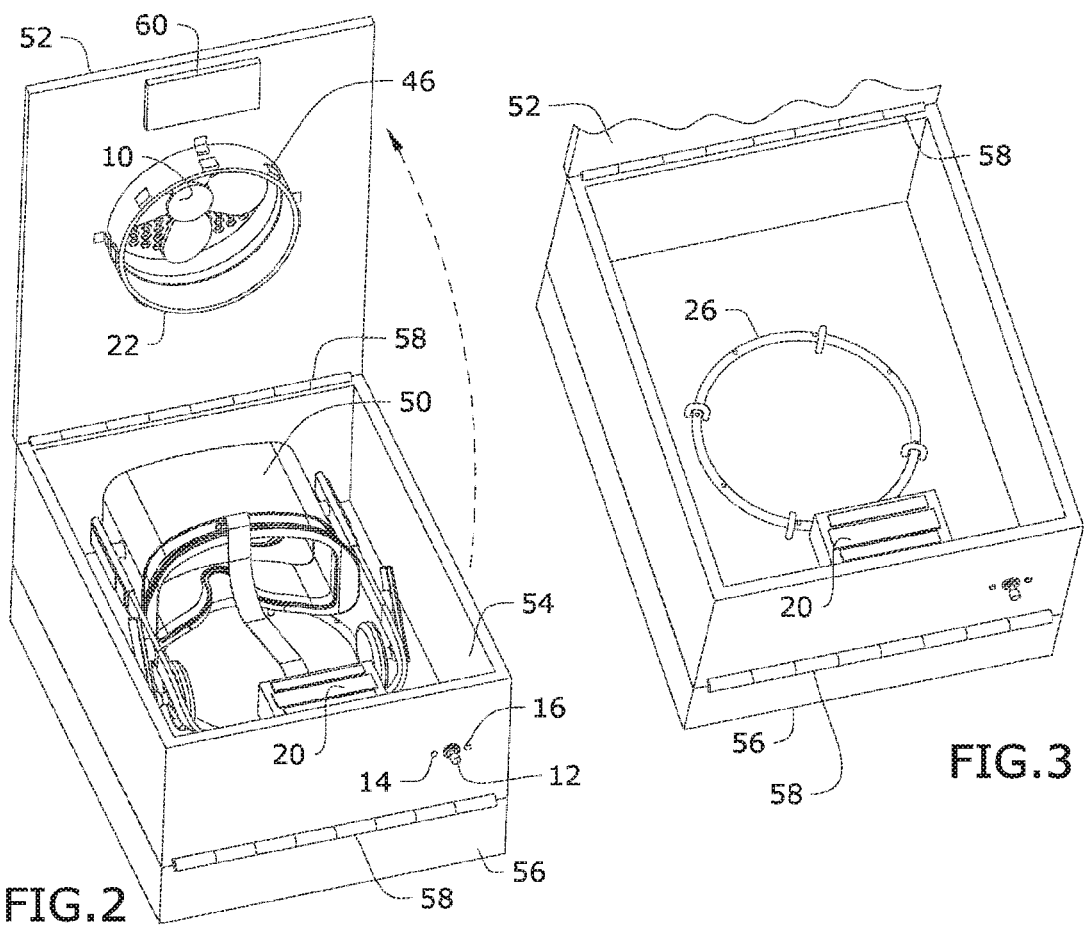

CLEANING AND DISINFECTING CRADLE FOR HEAD WORN ITEMS

CROSS REFERENCE TO RELATED APPLICATIONS

This application is a continuation of U.S. patent application Ser. No. 16/409,726 filed May 10, 2019, which is a continuation of U.S. patent application Ser. No. 15/720,037, filed Sep. 29, 2017, now U.S. Pat. No. 10,328,166, which claims benefit under 35 U.S.C. § 119(e) of U.S. Provisional Application having Ser. No. 62/402,827 filed Sep. 30, 2016, the entire contents of which are hereby incorporated by reference. This application is also related to International Application No. PCT/US2017/054342 filed concurrently on Sep. 29, 2017.

BACKGROUND

The embodiments described herein relate generally to headsets, and more particularly, to a cleaning and disinfecting cradle for virtual reality visors.

Virtual reality (VR) visors (head mounted displays) and other headsets have the same vulnerability when used in public demonstration venues. The visors connect directly to the face of the many individuals using them, making them a conduit for contagion (via contact, sneeze, etc.), as well as just general dirt and oils being passed from person to person.

Typically, visors are cleaned between uses by a human attendant wiping the visor with an alcohol wipe, which is prone to human error. Moreover, the wipe cannot reach all the crevices and nooks within a visor, allowing accumulations and contagions to build up.

Therefore, what is need is a device for sufficiently cleaning and disinfecting headsets, such as VR visors.

SUMMARY

In one aspect of the present disclosure, an apparatus for disinfecting and cleaning a headset comprises a chamber having an inner volume sufficient to accommodate the headset. A power supply may be coupled to the chamber. An ultraviolet (UV) light source may be coupled to the power supply. The UV light source is disposed to shine UV light onto a surface of the headset configured for placement against a face of a user to destroy bacteria and viruses on the surface. An air jet port may be coupled to a wall of the chamber. In addition, a closed-circuit air tube may be connected to the air jet port. The closed-circuit tube includes vents disposed to blow pressurized air around the headset to remove detritus from surfaces of the headset and dry the headset.

In another aspect, a system for disinfecting and cleaning headsets comprises a nanotech coating applied to a surface of a headset configured for placement against a face of a user. A chamber has an inner volume sufficient to accommodate the headset power supply may be coupled to the chamber. In addition, an ultraviolet (UV) light source may be coupled to the power supply. The UV light source is disposed to shine UV light onto the surface of the headset configured for placement against a face of a user to destroy bacteria or viruses.

BRIEF DESCRIPTION OF THE FIGURES

The detailed description of some embodiments of the present invention is made below with reference to the accompanying figures, wherein like numerals represent corresponding parts of the figures.

FIG. 1 is a front, perspective view of a chamber for cleaning and disinfecting items within the chamber according to an embodiment.

FIG. 2 is a top perspective view of the chamber of FIG. 1 with a lid raised showing the interior of the chamber with an item for cleaning/disinfecting placed inside.

FIG. 3 is a partial enlarged view of the chamber of FIG. 2 with the item removed from view.

DETAILED DESCRIPTION

Figure 4:
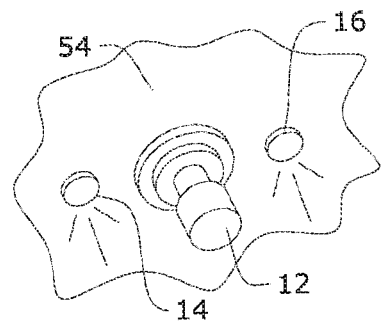
FIG. 4 is an enlarged partial view of a switch shown on the chamber of FIG. 2.
Figure 5:
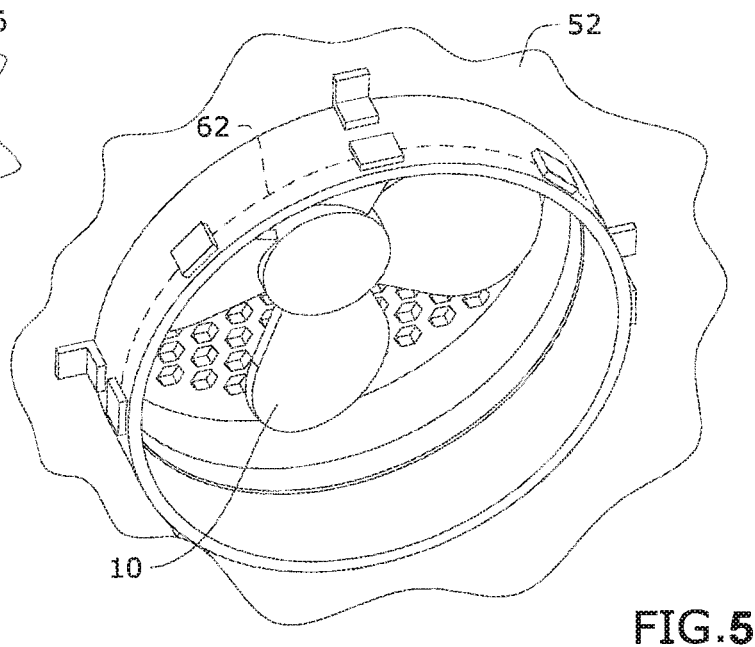
FIG. 5 is an enlarged partial view of a fan shown on the interior of the chamber of FIG. 2.
Figure 7:
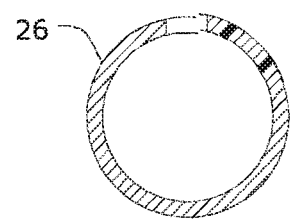
FIG. 7 is a cross-sectional view taken along the line 7-7 of FIG. 6.
Figure 6:
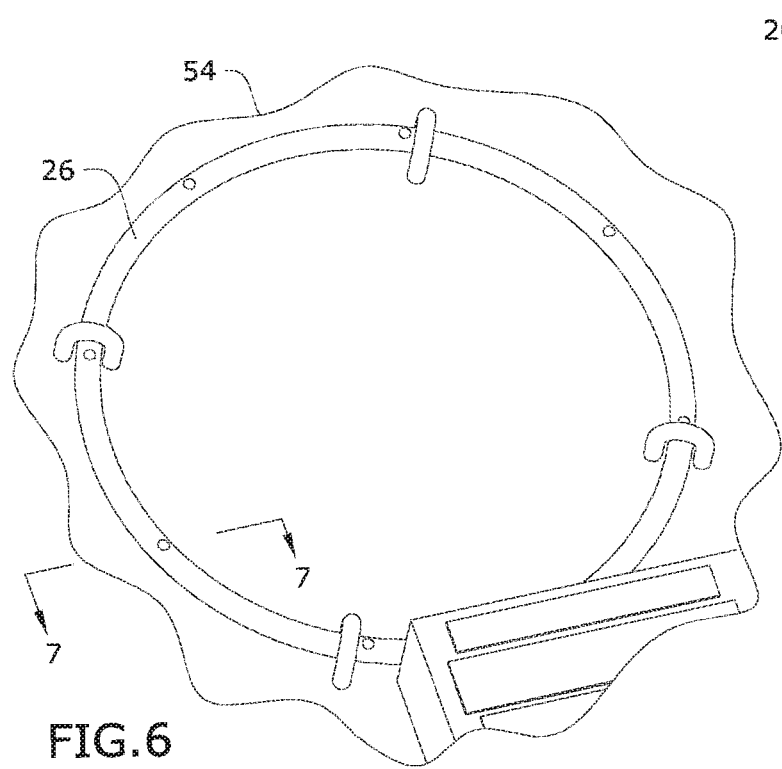
FIG. 6 is an enlarged partial view of a closed-circuit air tube shown on the interior of the chamber of FIG. 3.
Figure 8:
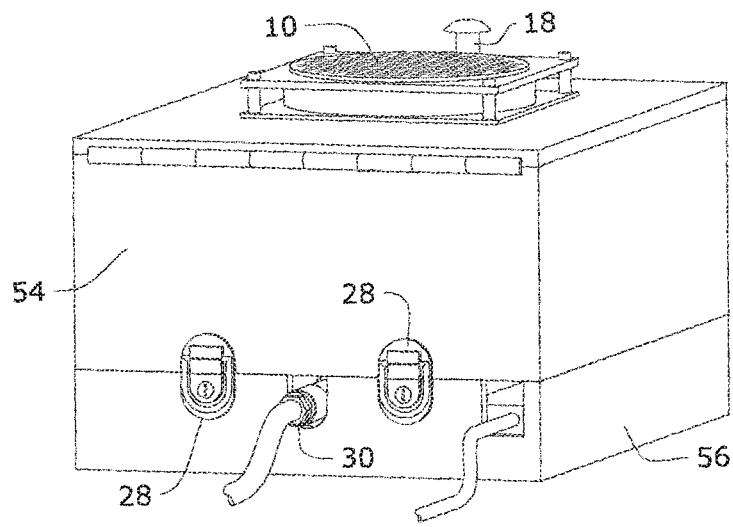
FIG. 8 is a rear perspective view of the chamber of FIG. 1.
Figure 9:
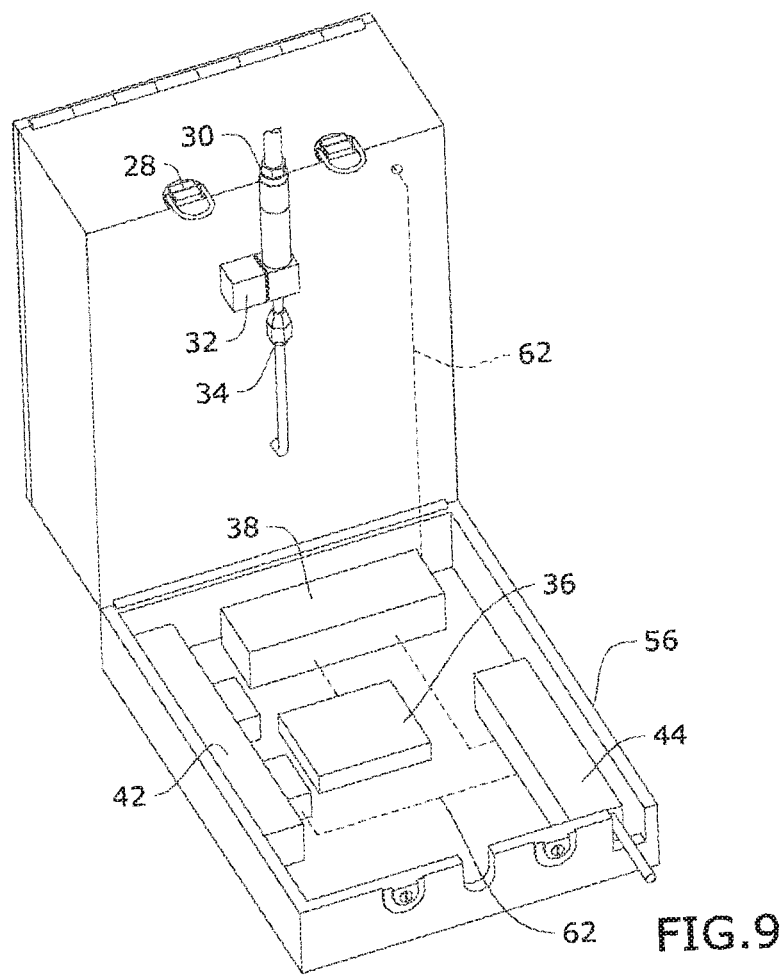
FIG. 9 is a top perspective view of the chamber of FIG. 1 with an upper compartment raised away from a lower compartment.

In the following detailed description of the invention, numerous details, examples, and embodiments of the invention are described. However, it will be clear and apparent to one skilled in the art that the invention is not limited to the embodiments set forth and that the invention can be adapted for any of several applications.

The device of the present disclosure may be used to clean and disinfect a variety of items and in particular, it will be appreciated that items worn by the person and re-worn by different people will find aspects of the present embodiments to be especially useful in application. For example, head worn gear such as visors, headsets, and glasses may be used amongst multiple people in for example, an amusement setting such as a virtual reality attraction or 3D movie. For sake of illustration, the following aspects will be described in the context of virtual reality (VR) applications, but it will be understood that other items that are worn multiple times and may need to be cleaned and/or disinfected may be used in embodiments of the subject disclosure without departing from the scope of invention.

By way of example, and referring to FIGS. 1-10, a system for cleaning and/or disinfecting items is shown according to an exemplary embodiment. In general, aspects of the system shown clean and/or disinfect items either singularly and by a combination using ultraviolet (UV) light, pressurized air, and an antibacterial coating.

For example, the system may include a chamber which in some embodiments works in tandem with a nanotech coating 55 applied to one or more surfaces of the item being cleaned. The nanotech coating may for example be applied to a surface that is designed to be in contact with a person's skin such as the face or around a user's temples. In FIG. 2, the nanotech coating 55 is applied to the inner seal of goggles that are part of a VR headset 50. The inner surface of the goggles is configured to contact against a user's face around the user's eyes when the headset is worn. As may be appreciated, this is a particularly sensitive area prone to spreading bacteria and viruses when the same item is passed on for use between people. The nanotech coating 55 isolates bacteria from each other, thus preventing biofilm creation and replication of viruses/bacteria. A UV light source 22 shines a disinfecting UV light onto at least the surfaces of the VR headset 50 that will contact users' faces. As may be appreciated, the nanotech coating 55 makes it easier for the UV light to destroy the bacteria and viruses while isolated.

In an exemplary embodiment, the chamber may be a box including a lid 52 attached via a hinge 58 to an upper compartment body 54. The upper compartment body 54 may be connected to a lower compartment body 56 via another hinge 58. The chamber may also include the UV light source 22, a closed-circuit air tube 26, and power supply 42 powering electrical components such as the UV light source 22. In an exemplary embodiment, the UV light source 22 may be attached to an interior side of the lid 52. The UV light source 22 may emit a UV-C spectrum light. In an exemplary embodiment, the UV light source 22 may be a ring-shaped body that is sized to fit within an inner circumference of the headset 50. The inner circumference may be defined by the open area between the surface of the headset 50 configured for placement against the face of the user and straps or arms of the headset 50 configured to secure the headset around the head of the user. The UV light source 22 may include a plurality of UV light emitting diodes (LEDs) 46 that are positioned on an outer surface of the ring-shaped body facing the inner circumference of the headset when the headset is placed into the chamber. In some embodiments, a ventilation fan 10 may be attached to the UV light source 22 to cool down the heat that is emitted by the LEDs 46 so that the UV light source does not overheat.

Figure 10:
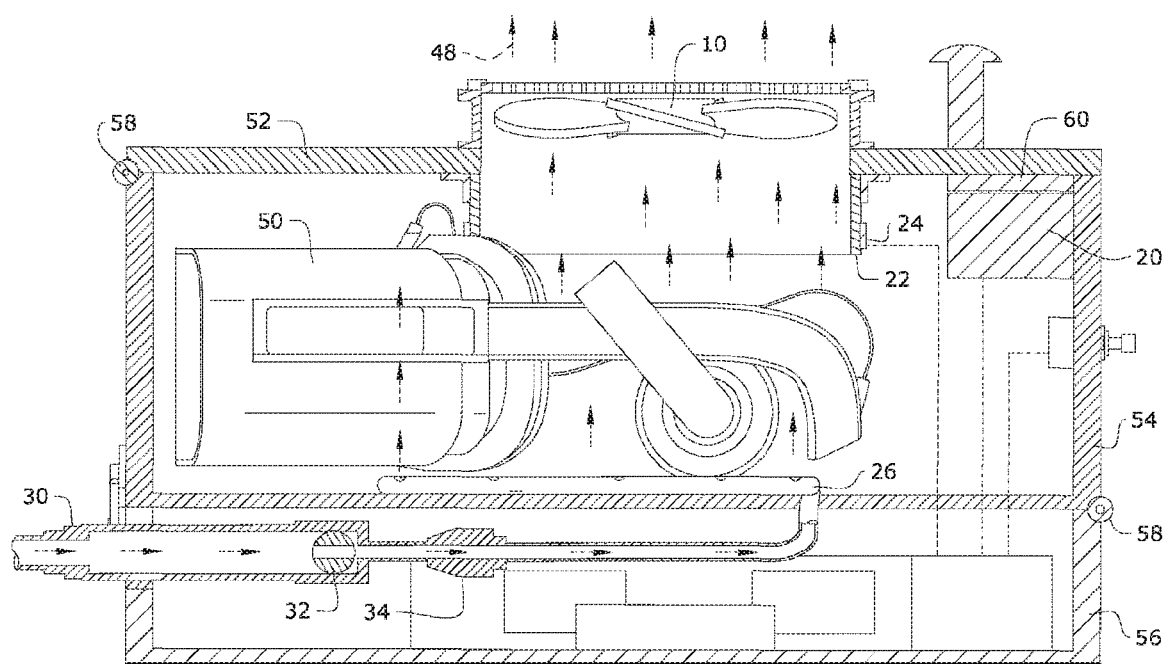
FIG. 10 is a cross-sectional view taken along the line 10-10 of FIG. 1.

The closed-circuit air tube 26 may be positioned on the floor of the chamber. The chamber may also include a quick-connect port 30 that connects a compressed air source (not shown) to the closed-circuit air tube 26 via a coupler 34. In some embodiments, pressurized air from the source into the air tube 26 is controlled by a CPU 36 actuating a solenoid valve 32 positioned between the port 30 and the closed-circuit tube 26. In an exemplary embodiment, the closed-circuit air tube 26 is substantially circular with a diameter that is approximately the same size or slightly less than the inner circumference of the headset 50. The closed-circuit air tube 26 may include a plurality of vents disposed to blow air directly at the headset 50 and in some embodiments, directly at the inner seal of the goggles. The flow of air is represented by arrows 48 as shown in FIG. 10.

In operation, the headset 50 may be positioned in the chamber so that the closed-circuit air tube 26 is under the headset 50. As the lid 52 is closed, the ring-shaped UV light source 22 fits within the inner circumference of the headset 50 so that the UV LEDs 46 may be within two inches or less of the headset 50 surfaces. In some embodiments, a switch 12 activates either the operation of the UV light source 22, the flow of compressed air through the closed-circuit air tube 26 or both. The UV light source 22 may destroy bacteria and viruses present on the surfaces of the headset 50. As will be appreciated, embodiments using UV-C based LEDs 46 with light distributed at close range are highly effective when used in close range (within two inches), thus reducing necessary time for disinfection and increasing the lifespan of the lights because they don't have to be activated as long. The headset 50 may then be subjected to air jet blasts through the vents of the closed-circuit air tube 26, which may knock free remaining detritus and sweat of previous users from the headset 50 surfaces and dry the surfaces so they are disinfected and ready for use by the next user. The compressed air may be pulsated through the vents in on/off intervals (such as 2 second intervals) for a predetermined period of time, such as 20 seconds by controlling the solenoid valve 32.

In some embodiments, operation of the UV light source 22 and/or blasts of the compressed air through the closed-circuit tube 26 may be automatically triggered by closing the lid 52. In some embodiments, the power supply 42 is connectable to a home based current source 44 (see FIG. 9). Wiring 62 may connect the power supply 42, to the fan 10, UV light source 22, the CPU 36, and the octocoupler 38. Power is routed to any of eight switches in the octocoupler 38 which prevents power from flowing through those switches to the end devices until the CPU 36 tells the octocoupler 38 to open specific gates and allow that power to flow. The lid 52 may be moved into open/closed positions by use of a handle 18. When the lid 52 is closed, a clasp(s) 28 may secure the box closed. Some embodiments may include a magnetic lock 20 that locks onto a metal plate 60. Wiring form the magnetic lock 20 and plate 60 may trigger a closed circuit signal that may be used to trigger the automatic operation of the system as described above. Some embodiments may include a ready light 14 indicating the system is ready for operation and/or an activation light 16 indicating the system is in the process of cleaning and/or disinfecting (see FIG. 4).

The above-described embodiments of the invention are presented for purposes of illustration and not of limitation. While these embodiments of the invention have been described with reference to numerous specific details, one of ordinary skill in the art will recognize that the invention can be embodied in other specific forms without departing from the spirit of the invention. Thus, one of ordinary skill in the art would understand that the invention is not to be limited by the foregoing illustrative details, but rather is to be defined by the appended claim.

What is claimed is:

1. An apparatus for disinfecting and cleaning a head worn item, comprising:
   a chamber having an inner volume sufficient to accommodate the head worn item; and
   an ultraviolet (UV) light source provided in the chamber, wherein the UV light source is disposed to shine UV light onto a surface of the head worn item configured for placement against a face of a user, wherein the UV light source comprises a ring-shaped body and includes a plurality of UV light emitting diodes (LEDs) positioned proximate a perimeter of the ring-shaped body.

2. The apparatus of claim 1, wherein the perimeter of ring-shaped body is sized to fit within an inner circumference of the head worn item defined by an open area between the surface of the head worn item configured for placement against the face of the user and straps or arms of the head worn item configured to secure the head worn item around a head of the user.

3. The apparatus of claim 2, wherein the UV LEDs are positioned on an outer surface of the ring-shaped body facing the inner circumference of the head worn item when the head worn item is placed into the chamber.

4. The apparatus of claim 1, further comprising:
   an air jet port coupled to a wall of the chamber; and
   a closed-circuit air tube connected to the air jet port, the closed-circuit tube including vents disposed to blow pressurized air around the head worn item to remove detritus from surfaces of the head worn item and dry the head worn item, wherein the vents of the closed-circuit air tube are positioned to blow directly at a portion of the surface of the head worn item configured for placement against the face of the user.

5. The apparatus of claim 1, wherein the ring-shaped body is sized to fit within the inner circumference of the head worn item.

6. An apparatus for disinfecting and cleaning a head worn item, comprising:
   a chamber having an inner volume sufficient to accommodate the head worn item; and
   an ultraviolet (UV) light source provided in the chamber, wherein the UV light source is disposed to shine UV light onto the surface of the head worn item configured for placement against a face of a user, wherein the UV light source comprises a ring-shaped body and includes a plurality of UV light emitting diodes (LEDs), wherein the ring-shaped body is sized to fit within the inner circumference of the head worn item.

7. The apparatus of claim 6, further comprising:
   an air jet port coupled to a wall of the chamber; and
   a closed-circuit air tube connected to the air jet port, the closed-circuit tube including vents disposed to blow pressurized air around the head worn item to remove detritus from the surface of the head worn item configured for placement against a face of a user and dry the head worn item.

8. The apparatus of claim 6, wherein the UV light source emits a UV-C type light.

9. The apparatus of claim 6, wherein the UV LEDs are positioned within two inches of the surface of the head worn item configured for placement against a face of a user when the head worn item is placed into the chamber.

10. The apparatus of claim 6, wherein the plurality of UV light emitting diodes (LEDs) are positioned proximate a perimeter of the ring-shaped body.

11. An apparatus for disinfecting and cleaning a head worn item, comprising:
   a chamber having an inner volume sufficient to accommodate the head worn item;
   an ultraviolet (UV) light source provided in the chamber, wherein the UV light source is disposed to shine UV light onto the surface of the head worn item configured for placement against a face of a user, wherein the UV light source comprises a ring-shaped body and includes a plurality of UV light emitting diodes (LEDs); and
   a ventilation fan attached to the UV light source to cool down the heat emitted by the LEDs.

12. The apparatus of claim 11, wherein the ring-shaped body is sized to fit within the inner circumference of the head worn item.

13. The apparatus of claim 11, wherein the plurality of UV light emitting diodes (LEDs) are positioned proximate a perimeter of the ring-shaped body.

* * * * *